US010502664B2

(12) United States Patent
Cardin

(10) Patent No.: US 10,502,664 B2
(45) Date of Patent: Dec. 10, 2019

(54) VACUUM-ASSISTED SAMPLE EXTRACTION DEVICE AND METHOD

(71) Applicant: ENTECH INSTRUMENTS INC., Simi Valley, CA (US)

(72) Inventor: Daniel B. Cardin, Simi Valley, CA (US)

(73) Assignee: Entech Instruments Inc., Simi Valley, CA (US)

(*) Notice: Subject to any disclaimer, the term of this patent is extended or adjusted under 35 U.S.C. 154(b) by 189 days.

(21) Appl. No.: 15/450,236

(22) Filed: Mar. 6, 2017

(65) Prior Publication Data
US 2017/0261408 A1 Sep. 14, 2017

Related U.S. Application Data

(60) Provisional application No. 62/305,468, filed on Mar. 8, 2016.

(51) Int. Cl.
G01N 1/20 (2006.01)
G01N 30/14 (2006.01)
(Continued)

(52) U.S. Cl.
CPC ............ *G01N 1/20* (2013.01); *G01N 1/2226* (2013.01); *G01N 30/06* (2013.01); *G01N 30/14* (2013.01);
(Continued)

(58) Field of Classification Search
CPC ........ G01N 1/20; G01N 1/2226; G01N 30/14; G01N 30/06; G01N 2001/2229;
(Continued)

(56) References Cited

U.S. PATENT DOCUMENTS 4,213,326 A 7/1980 Brodasky
4,849,179 A 7/1989 Reinhardt et al.
(Continued)

FOREIGN PATENT DOCUMENTS

CN 101793880 A 8/2010
CN 203324233 U 12/2013
(Continued)

OTHER PUBLICATIONS

International Search Report dated May 28, 2018, for PCT Application No. PCT/US2018/020313, six pages.
(Continued)

Primary Examiner — Marrit Eyassu
(74) Attorney, Agent, or Firm — Kubota & Basol LLP

(57) ABSTRACT

A sample extraction device and a desorption device for use in gas chromatography (GC), gas chromatography-mass spectrometry (GCMS), liquid chromatography (LC), and/or liquid chromatography-mass spectrometry (LCMS) are disclosed. In some examples, the sample extraction device includes a lower chamber holding a sorbent. The sample extraction device can extract sample headspace gas from a sample vial by placing the sorbent inside the vial and creating a vacuum to increase recovery of low volatility compounds, for example. Once the sample has been collected, the sample extraction device can be inserted into a desorption device. The desorption device can control the flow of a carrier fluid (e.g., a liquid or a gas) through the sorbent containing the sample and into a pre-column and/or a primary column of a chemical analysis device for performing GC, GCMS, LC, LCMS, and/or some other chemical analysis process.

16 Claims, 6 Drawing Sheets

(51) Int. Cl.
    *G01N 30/06*     (2006.01)
    *G01N 1/22*     (2006.01)
    *G01N 30/72*     (2006.01)
    *G01N 30/02*     (2006.01)
    *G01N 30/00*     (2006.01)

(52) U.S. Cl.
    CPC ....... *G01N 1/2214* (2013.01); *G01N 30/7206* (2013.01); *G01N 30/7233* (2013.01); *G01N 2001/2229* (2013.01); *G01N 2030/009* (2013.01); *G01N 2030/025* (2013.01); *G01N 2030/027* (2013.01); *G01N 2030/062* (2013.01); *G01N 2030/143* (2013.01)

(58) Field of Classification Search
    CPC ........... G01N 1/2214; G01N 2030/009; G01N 2030/027; G01N 2030/025; G01N 30/7233; G01N 30/7206; G01N 2030/062; G01N 2030/143
    USPC ...................................................... 73/863.23
    See application file for complete search history.

(56) References Cited

U.S. PATENT DOCUMENTS

| | | | |
|---|---|---|---|
| 5,363,707 A | | 11/1994 | Augenblick et al. |
| 5,496,741 A | | 3/1996 | Pawliszyn |
| 5,711,786 A | | 1/1998 | Hinshaw |
| 5,792,423 A | | 8/1998 | Markelov |
| 6,186,012 B1 | * | 2/2001 | Kenny .................... G01N 1/28 73/863.12 |
| 6,351,983 B1 | | 3/2002 | Haas et al. |
| 6,395,560 B1 | | 5/2002 | Markelov |
| 6,484,560 B1 | | 11/2002 | Prest |
| 6,662,626 B2 | | 12/2003 | van der Maas |
| 6,677,129 B1 | | 1/2004 | Blume |
| 6,770,246 B1 | | 8/2004 | Husek |
| 6,814,785 B2 | | 11/2004 | Tipler et al. |
| 7,464,614 B2 | * | 12/2008 | Harvey .................... G01N 1/22 73/863.84 |
| 7,776,615 B2 | | 8/2010 | Yuka et al. |
| 8,182,768 B2 | | 5/2012 | Tipler et al. |
| 8,404,185 B2 | | 3/2013 | Tipler et al. |
| 2002/0144949 A1 | | 10/2002 | Berger et al. |
| 2004/0072375 A1 | | 4/2004 | Gjerde et al. |
| 2005/0014156 A1 | * | 1/2005 | Pawliszyn ................ G01N 1/40 435/7.23 |
| 2005/0019950 A1 | | 1/2005 | Gjerde et al. |
| 2006/0137432 A1 | | 6/2006 | Kin et al. |
| 2006/0286606 A1 | * | 12/2006 | Oliver ....................... B01L 9/54 435/7.1 |
| 2007/0193871 A1 | | 8/2007 | Wiseman et al. |
| 2008/0064115 A1 | * | 3/2008 | Hiramatsu ............. B01D 15/00 436/178 |
| 2011/0277563 A1 | | 11/2011 | Scott et al. |
| 2012/0160038 A1 | | 6/2012 | Wells et al. |
| 2013/0017545 A1 | | 1/2013 | Yong et al. |
| 2014/0345365 A1 | | 11/2014 | Aono et al. |
| 2015/0075300 A1 | | 3/2015 | Hankemeier et al. |
| 2015/0276780 A1 | * | 10/2015 | Bremer .................. B01D 53/02 73/23.41 |
| 2015/0364310 A1 | * | 12/2015 | Musselman ............. H01J 49/16 250/282 |
| 2017/0284978 A1 | | 10/2017 | Cardin |
| 2017/0303900 A1 | | 10/2017 | Cardin |
| 2018/0246071 A1 | | 8/2018 | Cardin |

FOREIGN PATENT DOCUMENTS

| | | |
|---|---|---|
| CN | 104133031 A | 11/2014 |
| CN | 105866272 A | 8/2016 |
| CN | 106124255 A | 11/2016 |
| CN | 107085046 A | 8/2017 |
| EP | 0 572 968 A2 | 12/1993 |
| EP | 2 469 261 A1 | 6/2012 |
| EP | 3 040 721 A1 | 7/2016 |
| JP | 2015197444 A | 11/2015 |
| KR | 2004-0012068 A | 2/2004 |
| SU | 817583 A1 | 3/1981 |
| WO | WO-94/28409 A2 | 12/1994 |
| WO | WO-2008/020416 A2 | 2/2008 |
| WO | WO-2008/157074 A2 | 12/2008 |
| WO | WO-2008/157074 A3 | 12/2008 |
| WO | WO-2011/143349 A1 | 11/2011 |
| WO | WO-2017/156005 A1 | 9/2017 |
| WO | WO-2018/013946 A1 | 1/2018 |

OTHER PUBLICATIONS

International Search Report dated Jun. 1, 2017, for PCT Application No. PCT/US2017/021167, seven pages.

International Search Report dated Sep. 14, 2017, for PCT Application No. PCT/US2017/042172, six pages.

* cited by examiner

VACUUM-ASSISTED SAMPLE EXTRACTION DEVICE AND METHOD

CROSS-REFERENCE TO RELATED APPLICATIONS

This application claims the benefit of U.S. Provisional Patent Application No. 62/305,468, filed on Mar. 8, 2016, the entire disclosure of which is incorporated herein by reference in its entirety for all intended purposes.

FIELD OF THE DISCLOSURE

This relates to a sample extraction device and, more particularly, to a sample extraction device for use in various chromatography techniques such as gas chromatography (GC), gas chromatography-mass spectrometry (GCMS), liquid chromatography (LC) and/or liquid chromatography-mass spectrometry (LCMS).

BACKGROUND OF THE DISCLOSURE

GC, GCMS, LC and LCMS are techniques of performing analysis of trace chemicals in a wide range of sample matrices. In some examples, these techniques can be used to study biological matrices such as breath, blood, and urine; to study trace chemicals in food, water, and air; to detect odors in foods, beverages, products, and water supplies; and/or to analyze pharmaceuticals dissolved in water.

In some examples, samples for GC, GCMS, LC, and LCMS can be prepared using solvent extraction, also known as liquid-liquid extraction. Solvent extraction can include transferring one or more solutes from a feed solution to a solvent to form an extract, which can then be analyzed by GC, GCMS, LC, LCMS, or other analytical techniques, for example. In some examples, headspace analysis can be another approach for sample preparation and cleanup. Headspace analysis can include capturing the headspace gas contained in a sample vial holding a liquid or solid sample, for example. In some examples, the liquid or solid sample can fully or partially evaporate into the headspace gas so that when the headspace gas is captured, some or all of the sample is captured in a gaseous state. However, headspace analysis can traditionally suffer from poor sensitivity and limited volatility range due to the small gas phase sample size limitations of many techniques, the inability to concentrate or "enrich" the headspace compounds prior to instrumental analysis, and the inability to further extract chemicals out of the liquid or solid phase to enrich low volatility compounds. Thus, there exists a need for a device and method for quantitatively extracting samples for GC, GCMS, LC, or LCMS with improved sensitivity and volatility range.

SUMMARY OF THE DISCLOSURE

This disclosure relates to a sample extraction device and, more particularly, to a sample extraction device for use in various chromatography techniques such as gas chromatography (GC), gas chromatography-mass spectrometry (GCMS), liquid chromatography (LC) and/or liquid chromatography-mass spectrometry (LCMS). In some examples, the sample extraction device can be referred to as a Sorbent Pen. The sample extraction device can contain a sorbent configured to absorb or adsorb a sample. In some examples of the disclosure, the sample extraction device can be inserted into a sample vial to collect sample and/or headspace gas containing the sample. A vacuum can be drawn through an internal seal of the sample extraction device to facilitate rapid and thorough collection of the sample, for example. In some examples, the disclosed sample extraction techniques that occur under vacuum can be referred to as Vacuum-Assisted Sorbent Extraction, or VASE. In some examples, the sample collection device can be used at a higher pressure, such as atmospheric pressure, inside the sample vial or outside of the sample vial (e.g., to sample the air around the sample extraction device).

Once the sample has been extracted, the sample extraction device can be coupled to a chemical analysis device and chemical analysis (e.g., GC, GCMS, LC, or LCMS) can occur. The sample extraction device can allow the flow of a carrier fluid (e.g., a gas or a liquid) through a sorbent containing the sample, and into a pre-column and/or a primary column of a chemical analysis device configured to perform GC, GCMS, LC, LCMS, and/or some other sample analysis procedure.

DETAILED DESCRIPTION

In the following description, reference is made to the accompanying drawings which form a part hereof, and in which it is shown by way of illustration specific examples that can be practiced. It is to be understood that other examples can be used and structural changes can be made without departing from the scope of the examples of the disclosure.

This disclosure relates to a sample extraction device and, more particularly, to a sample extraction device for use in various chromatography techniques such as gas chromatography (GC), gas chromatography-mass spectrometry (GCMS), liquid chromatography (LC) and/or liquid chromatography-mass spectrometry (LCMS). In some examples, the sample extraction device can be referred to as a Sorbent Pen. The sample extraction device can contain a sorbent configured to absorb or adsorb a sample. In some examples of the disclosure, the sample extraction device can be inserted into a sample vial to collect sample and/or headspace gas containing the sample. A vacuum can be drawn through an internal seal of the sample extraction device to facilitate rapid and thorough collection of the sample, for example. In some examples, the disclosed sample extraction techniques that occur under vacuum can be referred to as Vacuum-Assisted Sorbent Extraction, or VASE. In some examples, the sample collection device can be used at a higher pressure, such as atmospheric pressure, inside the sample vial or outside of the sample vial (e.g., to sample the air around the sample extraction device).

Once the sample has been extracted, the sample extraction device can be coupled to a chemical analysis device and chemical analysis (e.g., GC, GCMS, LC, or LCMS) can occur. The sample extraction device can allow the flow of a carrier fluid (e.g., a gas or a liquid) through a sorbent containing the sample, and into a pre-column and/or a primary column of a chemical analysis device configured to perform GC, GCMS, LC, LCMS, and/or some other sample analysis procedure.

Figure 1A:
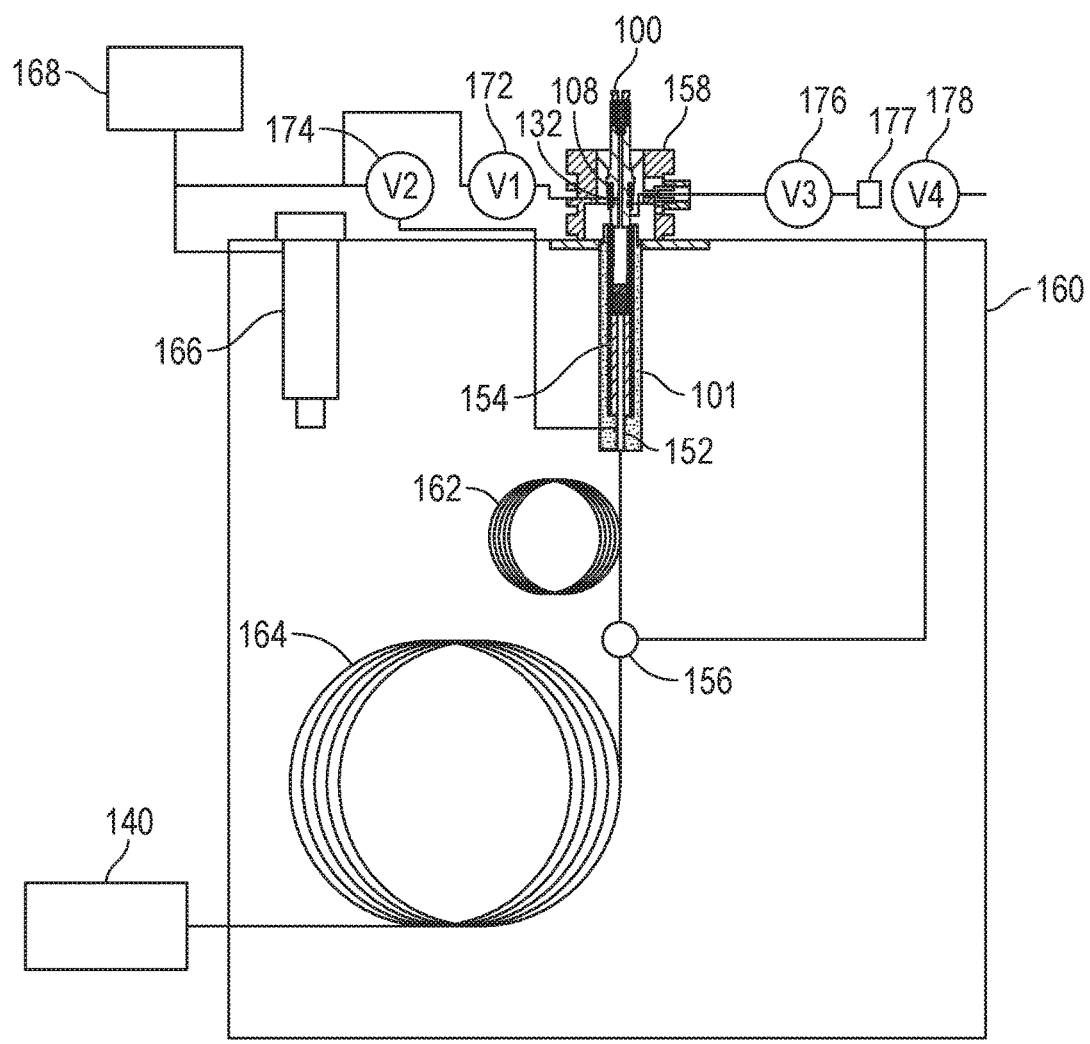
FIG. 1A illustrates an exemplary sample extraction device, an exemplary desorption device and an exemplary chemical analysis device for conducting chemical analysis according to examples of the disclosure.

FIG. 1A illustrates an exemplary sample extraction device 100 and an exemplary chemical analysis device 160 and detector 140 for conducting chemical analysis according to examples of the disclosure. In some examples, chemical analysis device 160 and detector 140 can correspond to a chromatograph configured to perform gas chromatography (GC), gas chromatography-mass spectrometry (GCMS), liquid chromatography (LC), liquid chromatography-mass spectrometry (LCMS) or some other form of chemical analysis, including other forms of chromatography (e.g., detector 140 can be a mass spectrometer for detecting samples passing through the chemical analysis device 160, such as a quadrupole mass spectrometer). The sample extraction device 100 can house a sample that was previously collected in a sample collection process, as will be described below with reference to FIGS. 2-3, for example.

In some examples, the chemical analysis device 160 can desorb sample from the sample extraction device 100 using a thermal desorber configuration that will now be described. Specifically, in some examples, the chemical analysis device 160 can include, divert vent 156, pre-column 162, primary column 164, injector 166, pressure controller 168, thermal desorption device 101 into which sample extraction device 100 can be inserted for desorbing sample into chemical analysis device 160, and a plurality of valves 172-178. In some examples, injector 166 can be a capped-off GC injector.

The desorption device 101 can be made of stainless steel and can optionally be lined with ceramic, and can include a replaceable liner 154 and heat sink 158. The replaceable liner 154 can improve transfer of sample from the sample extraction device 100 to the pre-column 162 and primary column 164 of chemical analysis device 160 without (or with minimal) chemical reactions, for example. Further, liner 154 can include channel 152 to fluidly couple the sample extraction device 100 to the chemical analysis device 160. In some examples, heat sink 158 can protect rubber seals 108 between the sample extraction device 100 and the desorption device 101 from excessive heat exposure and/or chemical outgassing. As an example, the rubber seals 108 can be included in the sample extraction device, as will be described below with reference to FIGS. 2A-2C.

In some examples, during the chemical analysis process (e.g., GC, GCMS, LC, or LCMS), the first valve 172 can control flow of a carrier fluid from pressure controller 168 through sorbent inside sample extraction device 100 for transfer of sample from the sample extraction device 100 to the pre-column 162 and primary column 164. The first valve 172 can be fluidly coupled to the sample extraction device 100 by way of port 132 of the sample extraction device 100, for example. Depending on the chemical analysis procedure and in the disclosed configuration, the carrier fluid can be a gas (e.g., for GC or GCMS), though it is understood that in some configurations, the carrier fluid can be a liquid (e.g., for LC or LCMS). The second valve 174 can control the flow of fluid around (e.g., bypassing) the sample extraction device 100 into channel 152 during preheating and can also be used to check for leaks between the sample extraction device 100 and desorption device 101, for example. In some examples, the third valve 176 can control flow of fluid (flowing into sample extraction device 100 via the first valve 172) directly out a split vent 177 to precisely and reproducibly reduce the amount of sample transferred to the pre-column 162 and primary column 164 and/or to increase sample injection rates into the chemical analysis device 160. The fourth valve 178 can control flow of fluid out from a divert vent 156 downstream of the pre-column 162 for either high flow pre-column enrichment without splitting, or back-flushing to prevent contamination of the primary column 164 with heavier contaminants, for example.

Upon desorption of the sample, the sample can pass through the pre-column 162 and the column 164 at a rate controlled by controller 168 by way of controlling the pressure of carrier gas. As the sample flows through the pre-column 162 and column 164, various compounds of the sample can move at different rates depending on compound mass, for example. In some examples, the sample can exit column 164 to enter the detector device 140, which can be used to identify the relative concentrations of compounds present in the sample based on time of arrival at the detector device 140 and by the mass fragmentation pattern of the compounds when using a mass spectrometer. In this way, the composition of the sample can be determined.

Figure 1B:
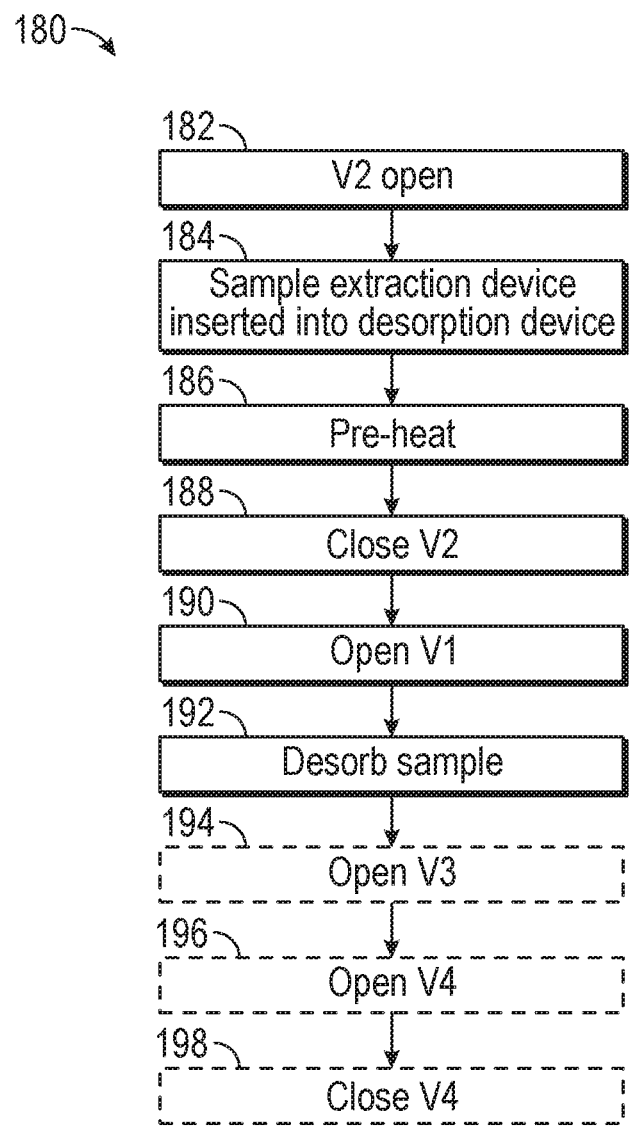
FIG. 1B illustrates an exemplary process for performing a chemical analysis procedure using a sample extraction device, desorption device, chemical analysis device, and detector according to examples of the disclosure.

FIG. 1B illustrates an exemplary process 180 for performing a chemical analysis procedure using sample extraction device 100, desorption device 101, chemical analysis device 160, and detector 140 according to examples of the disclosure. As an example, the chemical analysis process can be GCMS. To perform GCMS, the pressure controller 168 can supply a carrier gas, such as helium, nitrogen, or some other inert or non-reactive gas, which can flow through sorbent inside sample extraction device 100 and into pre-column 162 to facilitate sample extraction from the sorbent.

Initially, in step 182, the second valve 174 can be open, for example. In some examples, the sample extraction device 100 can be inserted into the desorption device 101 in step 184 while second valve 174 is open. Next, in step 186, a pre-heat can occur while second valve 174 is open. In some examples, the pre-heat can take zero to three minutes, though other lengths of time are possible. After the pre-heat, the second valve 174 can be closed in step 188 and the first valve 172, which can be fluidly coupled to the sample extraction device 100 by way of port 132 of the sample extraction device 100, can be opened in step 190. The closing of second valve 174 and the opening of first valve 172 can cause the desorption of the sample in step 192, for example. In some examples, at step 194, the third valve 176 can be opened to optionally perform a split injection. Performing a split injection can precisely and reproducibly reduce the amount of sample transferred to the column and increase injection rates, for example. In some examples, the third valve 176 is left open and the fourth valve 178 is opened in step 196 to improve transfer of heavy sample chemicals to the pre-column 162 while excess gas flows out from the fourth valve 178. Alternatively, in some examples, the third valve 176 can be left closed during sample desorption steps 192-196 to achieve complete transfer of heavy compounds into the pre-column 162. After desorption, if the fourth valve 178 had been opened in step 196, it can be closed in step 198, for example. The third valve 176 can open or remain open to remove any residual sample left in the sample extraction device 100 during a bake out process to clean the sample extraction device 100 for reuse in another sample analysis. In some examples, sample extraction device 100 can be reused hundreds of times in this way.

Figure 2A:
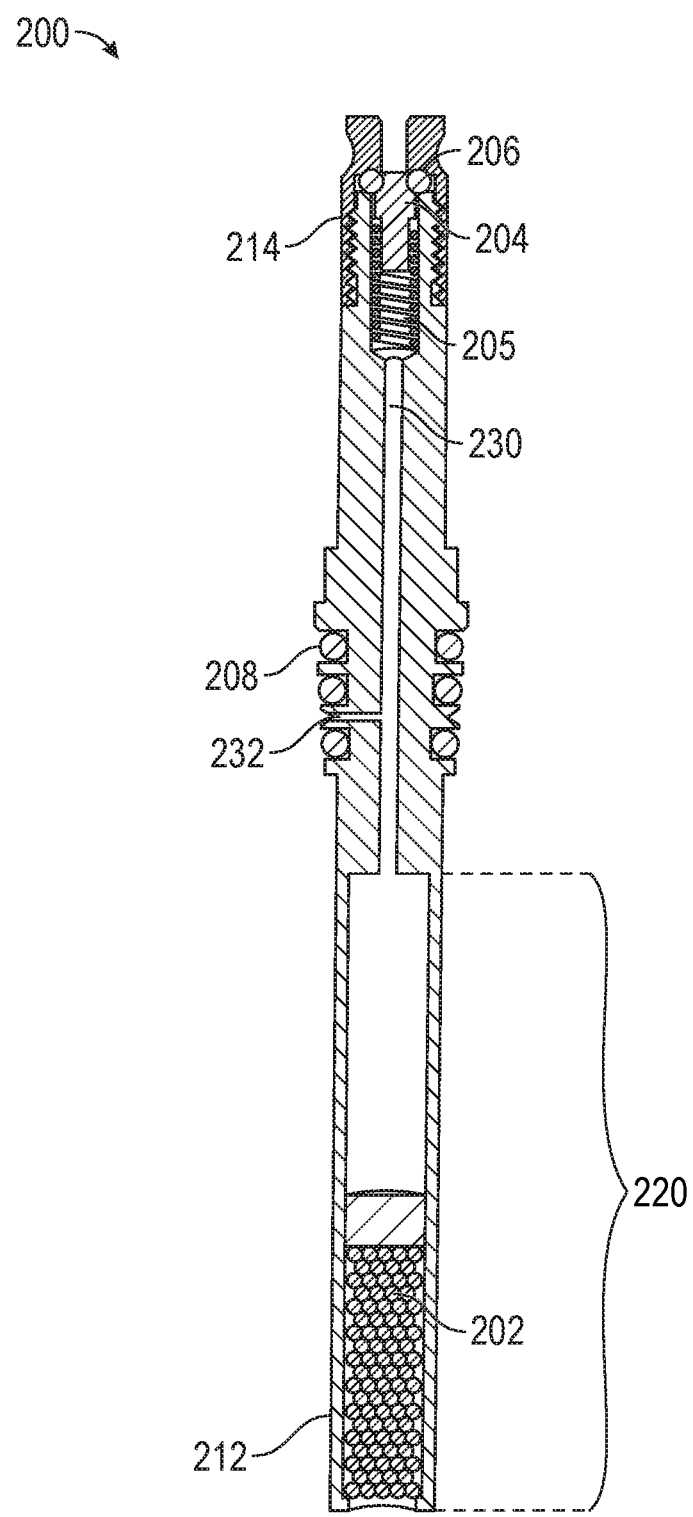
FIG. 2A illustrates an exemplary sample extraction device according to examples of the disclosure.

FIG. 2A illustrates an exemplary sample extraction device 200 according to examples of the disclosure. In some examples, sample extraction device 200 can correspond to sample extraction device 100 in FIGS. 1A-1B, and can be used for chemical analysis in a manner similar to that described with respect to FIGS. 1A-1B. As an example, sample extraction device 200 can have a diameter between 1/32 in. and 3/8 in. (e.g., the external or internal diameter of the sample extraction device); in some examples, the diameter of sample extraction device 200 can be as small as the diameters of the capillary columns (e.g., pre-column 162 and/or column 164) in the chemical analysis device. In some examples, other dimensions are possible. Sample extraction device 200 can comprise a tube-like structure, for example, that includes various channels and/or cavities as will be described below. In some examples, sample extraction device 200 can be fabricated from stainless steel or another suitable material (e.g., a material that is substantially inert). All or part of the surface of sample extraction device 200 can be coated with a chemical vapor deposition (CVD)-deposited ceramic to increase the inertness of the sample extraction device 200, for example. Other coatings that similarly increase the inertness of the sample extraction device 200 can similarly be used.

Sample extraction device 200 can include lower cavity 220. In some examples, the lower cavity 220 can contain a sorbent 202, which can be, for example, an adsorbent or an absorbent. The sorbent can be Tenax TA, Tenax/Carboxen, a short piece of 0.53 mm ID porous layer open tubular (PLOT) column ranging in composition from polydimethylsiloxane (PDMS), PLOT 0, and/or carboxen, or some other sorbent that can be chosen based on the sample(s) to be collected by the sample collection device 200, for example. As will be described below, in some examples, sorbent 202 can be selected to collect a sample for analysis. In some examples, the sorbent 202 can be located towards an extraction end 212 of the sample extraction device 200. That is to say, sorbent 202 can be closer to the extraction end 212 of the sample extraction device 200 than it is to a valve end 214 of the sample extraction device. Extraction end 212 of the sample extraction device 200 can be open to the environment of the sample extraction device such that the sample being collected can enter lower cavity 220, and can adsorb or absorb to sorbent 202, as will be described in more detail below.

At the valve end 214 of the sample extraction device 200 (e.g., opposite extraction end 212 of the sample extraction device 200), the sample extraction device 200 can include a sealing plunger 204, a spring 205, and an internal seal 206, for example. The internal seal 206 can be a fluoroelastomer seal, a perfluoroelastomer seal, or any other suitable seal, for example. In some examples, sealing plunger 204 and internal seal 206 can selectively restrict fluid (e.g., gas, liquid, etc.) flow through internal channel 230 between sealing plunger 204/internal seal 206 and lower cavity 220/sorbent 202. For example, when sealing plunger 204 is pressed up against seal 206, fluid flow through sample extraction device 200 can be restricted, and when sealing plunger 204 is moved away or otherwise separated from seal 206, fluid flow through sample extraction device 200 may be unrestricted. In some examples, sealing plunger 204 can be tensioned via spring 205 against seal 206 such that in a default configuration, sealing plunger 204 can be pressed up against seal 206 and fluid flow through sample extraction device 200 can be restricted. In some examples, spring 205 can be fabricated from a non-reactive material, such as 316 stainless steel coated with a ceramic material using a chemical vapor deposition (CVD) process. Fluid flow (e.g., air being drawn into a vacuum source) through sample extraction device 200 can be allowed by causing sealing plunger 204 to move away from seal 206 (e.g., via mechanical means such as a pin from above, or other means). For example, a vacuum source can be coupled to the sample extraction device 100 at the valve end 214 to open sealing plunger 204 and draw a vacuum through sealing plunger 204, an internal channel 230, and lower cavity 220. Additionally, in some examples, sealing plunger 204 can remain open (e.g., during continuous vacuum evacuation) to evaporate unwanted matrix, such as water or alcohol, from the sample through sorbent 202.

As an example, during a sample extraction process in which a sample can be collected in sample extraction device 200, as will be described in more detail below, a vacuum can be drawn through sealing plunger 204, internal channel 230 and lower cavity 220 to facilitate sample collection by sorbent 202 in lower cavity 220. In some examples, after the sample has been collected by sample extraction device 200, the sealing plunger 204 can be opened to release the vacuum. However, releasing the vacuum by opening sealing plunger 204 can cause air to be pushed through sorbent 202. Thus, in some examples, the vacuum is not released via sealing plunger 204—rather, the sample extraction device 200 can simply be removed from the environment containing the sample (e.g., a sample vial) without releasing the vacuum, which can prevent air from entering the sorbent 202 and prevent backflushing of the sorbent 202 which can cause loss of adsorbed/absorbed compounds. Additionally, in some examples, after the sample has been collected by the sample extraction device 200, the sealing plunger 204 can be remain closed (e.g., as it can be during sample collection) and can isolate the sample from the environment, allowing the sample to be stored in the sample extraction device 200 between extraction and analysis. For example, spring 205 can cause the sealing plunger 204 to remain closed in the absence of a mechanical force to open sealing plunger 204. During storage, the sample extraction device 200 can be kept in an isolation sleeve to avoid contaminating the sample. Subsequently, in some examples, during the chemical analysis process, a carrier fluid can be drawn through sealing plunger 204, into internal channel 230 and lower cavity 220, and into chemical analysis device 160, allowing for rapid desorption of the sample from sorbent 202 into the chemical analysis device 160. Additionally or alternatively, in some examples, during the chemical analysis process, the carrier fluid can be drawn through port 232 (e.g., instead of through sealing plunger 204), into internal channel 230 and lower cavity 220, and into chemical analysis device 160. In some examples, port 232 can be a channel in fluid communication with lower cavity 220 and the outside of sample extraction device 200. Preferably, the open end of port 232 can be located between external seals 208 so that port 232 can be sealed when the sample extraction device 100 is sealed against another object (e.g., a desorption device or sample vial), for example. In some examples, other locations on sample extraction device 200 are possible.

The sample extraction device 200 can further include one or more external seals 208, for example. The external seals 208 can be made of an elastomeric material and can be fluoroelastomer seals or perfluoroelastomer seals. In some examples, the external seals 208 can be Viton™ seals or other suitable seals. The external seals 208 can be located externally on sample extraction device 200 between ends 212 and 214. The external seals 208 can include one or more gaskets or o-rings fitted around the outside of the sample extraction device 200, for example. In some examples, the external seals 208 can be used to form a seal between sample extraction device 200 and a sample vial into which sample extraction device 200 can be inserted during a sample extraction process (which will be described with reference to FIG. 2B), and/or to form a seal between sample extraction device 200 and desorption device 101 into which sample extraction device 200 can be inserted during a sample desorption process (as described previously).

Figure 2B:
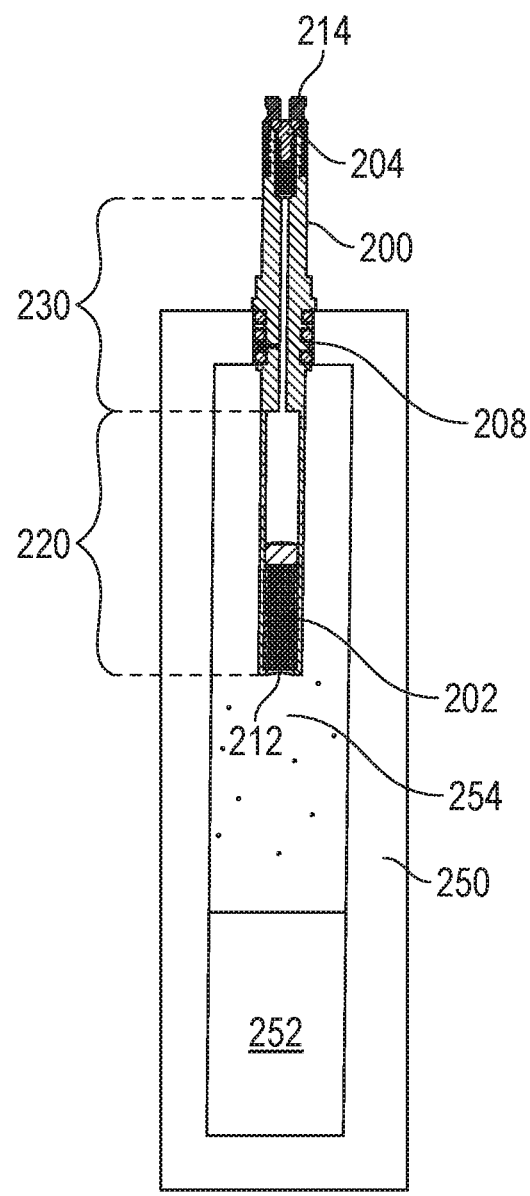
FIG. 2B illustrates an exemplary sample extraction device extracting a sample from a sample vial according to examples of the disclosure.

FIG. 2B illustrates an exemplary manner of extracting a sample from a sample vial 250 that includes sample 252 using sample extraction device 200 according to examples of the disclosure. In some examples, sample vial 250 can include a wall with a void into which sample extraction device 200 can be inserted, as shown (e.g., partially inserted into sample vial 250 such that extraction end 212 of sample extraction device 200 is inside sample vial 250, and valve end 214 of sample extraction device 200 remains outside of sample vial 250). Insertion of sample extraction device 200 into sample vial 250 can create a seal, at external seals 208, between sample extraction device 200 and sample vial 250 such that vacuum can be maintained inside sample vial 250 while sample extraction device 200 is inserted into sample vial 250. Sample vial 250 can contain a sample 252 and headspace gas 254, for example. Headspace gas 254 can include one or more compounds evaporated from sample 252. In some examples, sample 252 can be a liquid sample or a solid sample. Sample extraction device 200, seals 208, sample vial 250 and/or sample 252 can be configured such that when sample extraction device 200 is inserted into sample vial and sealed against sample vial 250, extraction end 212 of sample extraction device 200 can be positioned within headspace gas 254, above sample 252 (e.g., not positioned inside sample 252).

In some examples, while the sample extraction device 200 is inserted into sample vial 250, a vacuum can be pulled in sample vial 250 through the sample extraction device 200 by way of internal sealing plunger 204 (e.g., vacuum can be pulled through internal sealing plunger 204, internal channel 230 and lower cavity 220 containing sorbent 202). By pulling the vacuum through the sample extraction device 200 in this way, the evacuated headspace gas 254—which, in some examples, can include the sample of interest—can be absorbed or adsorbed by sorbent 202 in sample extraction device 200, as opposed to being lost as a result of by pulling vacuum in some other way (e.g., through a separate opening of the sample vial 250). In some examples, most (e.g., 99 percent or more) of the sample 252 can be in the solid or liquid phase when the vacuum is drawn, meaning the vacuum can mostly draw air, rather than evaporated sample, through sorbent 202. Thus, in some examples, it can be beneficial to draw vacuum via sample extraction device 200, remove the vacuum source, and leave extraction device 200 inside sample vial 250 in the vacuum-drawn state for a period of time to collect sample 252 in sorbent 202, as will be described in more detail below. The sample extraction device 200 can continue to hold the vacuum after the vacuum source is released, as previously described. During this time, the sample can continue to enter the gas phase and be collected by sorbent 202, as will now be described.

A vacuum source can pull the vacuum through the sample extraction device 200 for about 10-60 seconds, for example. The external seals 208 and internal seal 204 of the sample extraction device 200 can hold the vacuum even after the vacuum source has been removed. In some examples, the reduced pressure inside sample vial 250 can cause the sample 252 to enter the gas phase more quickly, allowing for faster sample 252 extraction into sorbent 202 compared to collection of sample 252 at higher pressures. Specifically, once under vacuum, sample 252 can, via diffusion, find its way to sorbent 202. Many compounds can be more than 99% in the liquid or solid phase while the vacuum is being drawn and later enter the gas phase under the vacuum held by sample extraction device 200, for example. Once in the gas phase, the sample can enter the sample extraction device 200 and remain trapped by the sorbent 202. In some examples, the sample extraction device 200 can remain in the sample vial 250 holding a vacuum and extracting sample for anywhere from a few minutes to several days (e.g., 10 minutes to 1-2 days). The evaporation and collection of the sample can occur more quickly under vacuum than it would under atmospheric or other elevated pressures. Additionally, in some examples, sample extraction can be performed at elevated temperatures (e.g., 25° C. or 100° C.) to further improve extraction times. Such ability to extract sample 252 using sample extraction device 200 under vacuum for extended periods of time can allow significant sample 252 to build up in sorbent 202, which can allow sample extraction device 200 to collect, and subsequent chemical analysis processes to detect, sufficient amounts of even very low-level compounds in sample 252.

A number of factors can be considered in selecting extraction temperature and extraction time for a given sample. For example, some compounds have a low vapor pressure and a high boiling point and may be extracted at a higher temperature and/or for a longer time than compounds with a higher vapor pressure and a lower boiling point. In some examples, "exhaustive extraction" can be performed in which the vacuum is held in the sample vial 250 and extraction is allowed to occur until all volatile chemicals have been extracted from sample 252. "Exhaustive extraction" can be highly reproducible because the liquid or solid sample 252 can be weighed prior to extraction, and several trials can be prepared using the same weight of sample.

Extracting sample under vacuum using sample extraction device 200 can have several advantages. For example, vacuum extraction performed over a long integration time can better recover low-volatility compounds than possible by other methods. Additionally, the diffusive sample extraction process disclosed herein (i.e., extracting sample 252 under vacuum conditions) can improve recovery of heavy compounds (e.g., improved ability to desorb those compounds from sorbent 202 into the chemical analysis device or otherwise) due to reduced channeling into the sorbent 202, as compared to methods that rely on a carrier gas to deliver the sample to a sorbent bed. Additionally, performing sample extraction under vacuum as described (e.g., such that sample 252 has transitioned to the gas phase and is under vacuum) can allow molecules of sample to find the extraction end 212 of sample extraction device 200 (and thus sorbent 202) much faster than they would otherwise in non-vacuum conditions, increasing the rate of extraction, due to reduced gas phase collisions resulting in faster net diffusion rates in the sample vial 250. In some examples, the vacuum extraction of the disclosure can allow recovery of heavier compounds without applying heat during the sample extraction process, allowing natural and biological samples to be analyzed without breakdown of the sample, which can produce artifacts that were not in the original sample. Samples such as foods, beverages, blood, urine, breath condensate, and other samples that may not tolerate elevated temperatures can be sampled by vacuum extraction at room temperature or another non-elevated temperature, for example.

In some examples, the sample collected using the vacuum-assisted extraction techniques and sample extraction device 200 of the disclosure can remain captured towards the outermost edge of the sorbent 202 (i.e., proximate to the edge of sorbent 202 directly exposed to sample 252 at the extraction end 212 of the sample extraction device 200), rather than being driven deep into sorbent 202 due to dynamic extraction of sample pulled into sorbent 202 via gas flow. This tendency of the sample to remain captured towards the outermost edge of sorbent 202 can cause the sample to be desorbed into the desorption device 101 and/or chemical analysis device 160 more rapidly, as compared to a sample that is more evenly distributed through sorbent 202, for example. Further, this tendency can ensure more complete desorption of sample/compounds from sorbent 202, making it easier to reuse the sample extraction device 200 without risk of cross-contamination and/or carryover between uses. In some examples, the tendency of the sample to collect at the opening of the extraction end 212 of the sample extraction device 200 can keep the sample extraction device 200 cleaner, preventing thermal breakdown of the sample during desorption, thus increasing the number of reuses of the sample extraction device 200. Lastly, the sample extraction device 200 can hold large amounts of sorbent 202, thus reducing analytical variability even with moderate matrix-related affinity differences of sample compounds to the liquid or solid sample 252.

While optimal sample extraction may be performed under vacuum or lower-pressure conditions, in some examples, passive sample extraction can be performed using sample extraction device 200 in non-vacuum conditions inside sample vial 250, and can even be performed outside of the sample vial 250 to sample air, for example. Some of the sample extraction techniques of this disclosure that utilize sample extraction device 200 can occur without the use of solvents, making the disclosed extraction techniques "green" (e.g., environmentally friendly).

Once the sample 252 is collected in sorbent 202 inside sample extraction device 200, chemical analysis (e.g., GC, GC-MS, or LC) can be performed to determine the composition of the sample, as described herein, for example. As described above, the sample extraction techniques of this disclosure can occur "off-line" from the chemical analysis device 160 (e.g., performed outside and independent of the chemical analysis device 160), thus making sample extraction time independent of the time it takes to analyze the sample in the chemical analysis device 160. Therefore, sample preparation can occur remotely from the chemical analysis device 160, allowing for longer extraction times as needed and for the extraction and analysis to occur in different locations as needed. This flexibility in when and where extraction can occur can allow extraction to be optimized, thus improving the sensitivity and versatility of the sample extraction device 200, for example. Additionally, in some examples, the sample collected by sorbent 202 can be stored in the sample extraction device 200 for some time before analysis occurs.

Figure 2C:
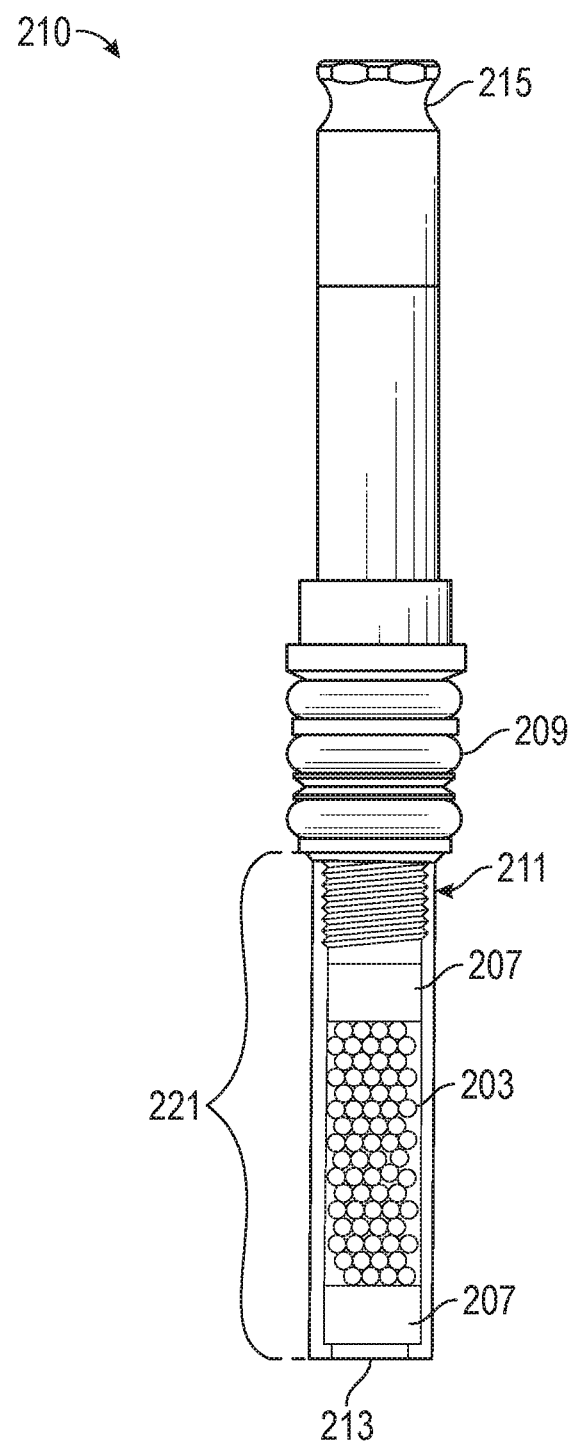
FIG. 2C illustrates another exemplary sample extraction device according to examples of the disclosure.

FIG. 2C illustrates another exemplary sample extraction device 210 according to examples of the disclosure. In some examples, sample extraction device 210 can be similar to sample extraction device 200 and can correspond to sample extraction device 100 in FIG. 1A to be used in a chemical analysis process similar to that described with respect to FIGS. 1A-1B. Sample extraction device 210 can include similar components to sample extraction device 200, such as external seal 209, lower cavity 221 with sorbent 203, extraction end 213, and a valve end 215, and can include various components of sample extraction device 200 not illustrated in FIG. 2C (e.g., sealing plunger 204 for pulling vacuum and/or selectively allowing solvent flow through the sample extraction device 210, spring 205, and internal seal 206), except as otherwise described here. In some examples, sample extraction device 210 can be used to extract samples that require LC or LCMS because they are not stable on a GC or GCMS column, and/or to extract samples that are better recovered using a solvent, rather than via thermal desorption prior to GC or GCMS. Accordingly, sample extraction device 210 can be used when sample from sample extraction device 210 is to be recovered using a solvent, whether for GC, GCMS, LC, and/or LCMS, for example. Because sample extraction device 210 can be used in conjunction with solvent, as described above, sorbent 203 can be a solvent-compatible sorbent.

In addition to components in common with sample extraction device 200, sample extraction device 210 can include threads 211 via which lower cavity 221 (including sorbent 203) can be attached to the remainder of the sample extraction device 210, and/or sorbent retention means 207, for example. In some examples, sorbent retention means 207 can be one or more screens, frits, or seals between which sorbent 203 can be contained in lower cavity 221, and which can confine sorbent 203 within lower cavity 221 such that sorbent 203 will not be expelled from sample extraction device 210 during solvent-extraction of the sample from the sample extraction device 210. As such, sorbent retention means 207 can be solvent-transmissive but not sorbent-transmissive. After sample extraction from sorbent 203 using a solvent (e.g., after the sample has been extracted for analysis by GC, GCMS, LC, and/or LCMS), the lower cavity 221 (including sorbent 203) can be removed for solvent extraction by decoupling the lower cavity 221 from the rest of the sample extraction device 210 at the threads 211. Solvent extraction can be conducted manually or in an automated manner, for example. In some examples, automated extraction can occur simultaneously with or sequentially with GC, GCMS, LC, and/or LCMS analysis.

Figure 3:
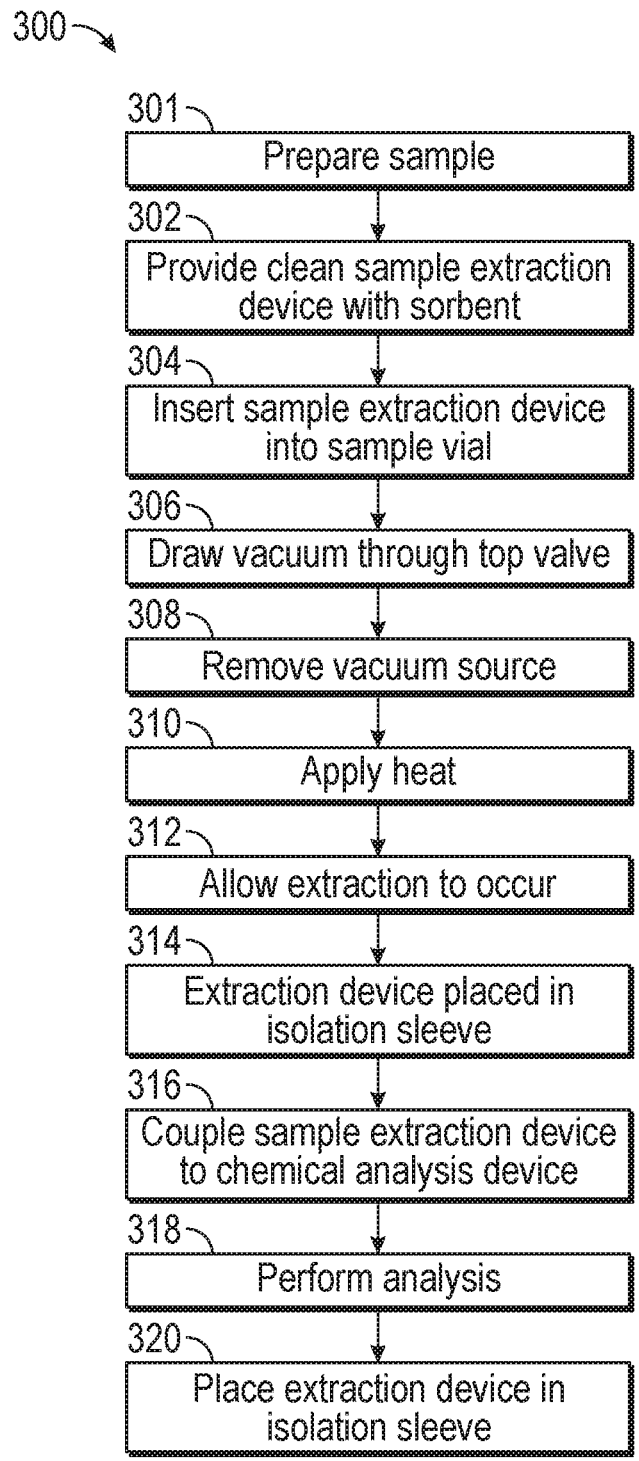
FIG. 3 illustrates an exemplary process for collecting a sample and conducting chemical analysis of the sample according to examples of the disclosure.

FIG. 3 illustrates an exemplary process 300 for collecting a sample and conducting chemical analysis of the sample according to examples of the disclosure. In some examples, in step 301 of process 300, the sample can be prepared. Preparing the sample can include weighing the sample into the sample vial (e.g., sample vial 250) and placing an appropriate cap and lid on the sample vial to allow insertion of a sample extraction device (e.g., sample extraction device 100, 200, or 210) into the sample vial, for example. In some examples, in step 302, the clean sample extraction device can be provided with a sorbent (e.g., sorbent 202).

Next, in step 304, the sample extraction device can be inserted into and coupled to a sample vial (e.g., sample vial 250) that includes a sample (e.g., sample 252), allowing the sample to be extracted from the sample vial into the sample extraction device. The sample extraction device can be sealed to the sample vial by an external seal (e.g., external seal 208) of the sample extraction device, for example. In some examples, in step 306, a vacuum can be drawn in the sample vial through a valve (e.g., sealing plunger 204), and thus via internal channel (e.g., internal channel 230) and lower cavity (e.g., lower cavity 220)—which can include a sorbent (e.g., sorbent 202)—of the sample extraction device. To draw the vacuum, a vacuum source can be coupled to the top (e.g., valve end 214) of the sample extraction device, for example. Next, in step 308, after enough time has passed to create a vacuum in the sample vial, the vacuum source can be removed. In some examples, during step 308, even after sufficient vacuum is reached, the vacuum source can remain coupled to sample extraction device and evacuation of the sample vial can continue for a period of time to boil off some of the matrix in the sample (e.g., water or alcohol). After the vacuum source is removed, the vacuum can be held by the sample extraction device (e.g., using internal seal 206 and external seals 208). In some examples, in step 310, heat can be applied to the sample vial (e.g., in some examples, anywhere from 4 degrees Celsius to 150 degrees Celsius, and typically 25 degrees Celsius).

In some examples, steps 304 and/or 306 can be skipped; for example, rather than being coupled to a sample vial, the sample extraction device can collect a sample from the surrounding air (e.g., the air in the environment of the sample extraction device); in some examples, the sample extraction device can be coupled to the sample vial and sample can be collected at atmospheric pressure in the sample vial—that is, step 306 can be skipped. In some cases of air analysis for indoor or outdoor air monitoring, the sample extraction device can collect sample for up to two weeks to determine an average concentration of chemicals in the air.

Once the extraction process has been set up (e.g., by applying a vacuum and/or heat, or by exposing the sample extraction device to air to be sampled), extraction can be allowed to occur in step 312. In some examples, the sample vial can remain under vacuum and applied heat for a predetermined amount of time, or until "exhaustive extraction" occurs. For example, the process can remain at step 312 for anywhere from one minute to two days depending on the compounds to be analyzed. After the sample is collected in the sample extraction device, the sample extraction device can be placed in an isolation sleeve at step 314 to prevent contamination of the sample during storage. Later, at step 316, the sample extraction device can be coupled to a chemical analysis device (e.g., chemical analysis device 160). At step 318, fluid can be flowed through the sample extraction device, including through the lower cavity of the sample extraction device, which includes the collected sample and a sorbent, to facilitate desorption of the sample into the chemical analysis device, which can perform GC, GCMS, LC, LCMS, or some other analysis procedure to evaluate one or more characteristics of the sample, such as its composition. After chemical analysis is complete, the sample extraction device can be placed in an isolation sleeve at step 320 so that it remains clean until the next extraction.

As such, the examples of the disclosure provide an improved sample extraction device and method for extracting sample from, for example, a liquid or solid contained in a sample vial, and desorbing such sample into a chemical analysis device for analysis.

Therefore, according to the above, some examples of the disclosure are related to a cavity configured to contain a sorbent, the cavity having an opening at an extraction end of the sample extraction device; and an internal seal configured to selectively restrict fluid flow through the cavity, the internal seal disposed at a valve end of the sample extraction device. Additionally or alternatively, in some examples, the sorbent is disposed within the cavity such that it is closer to the opening at the extraction end of the sample extraction device than it is to a valve end of the cavity. Additionally or alternatively, in some examples, the sample extraction device further comprises an external seal disposed around an outside of the sample extraction device. Additionally or alternatively, in some examples, the external seal comprises a fluoroelastomer seal or a perfluoroelastomer seal. Additionally or alternatively, in some examples, the external seal is configured to form a seal between the sample extraction device and a sample vial into which the sample extraction device is inserted. Additionally or alternatively, in some examples, the internal seal is configured to facilitate pulling vacuum in the sample vial through the cavity and the sorbent, the vacuum pulled by a vacuum source coupled to the sample extraction device at the valve end. Additionally or alternatively, in some examples, the internal seal is configured to facilitate pulling headspace gas that is inside the sample vial into the cavity and the sorbent. Additionally or alternatively, in some examples, the external seal is disposed at a location on the sample extraction device such that, when the sample extraction device is inserted into the sample vial, the extraction end of the sample extraction device is inside a headspace gas in the sample vial. Additionally or alternatively, in some examples, the internal seal maintains a vacuum inside the sample vial after removal of the vacuum source from the sample extraction device. Additionally or alternatively, in some examples, the external seal is configured to form a seal between the sample extraction device and a chemical analysis device into which the sample extraction device is inserted. Additionally or alternatively, in some examples, the internal seal is configured to facilitate flowing fluid through the cavity and the sorbent and into the chemical analysis device. Additionally or alternatively, in some examples, the sample extraction device further comprises a port configured to facilitate flowing fluid through the cavity and the sorbent and into the chemical analysis device. Additionally or alternatively, in some examples, the internal seal is configured to isolate sample, collected in the sorbent, from an environment of the sample extraction device after a sample extraction process. Additionally or alternatively, in some examples, the cavity is removably coupled to the sample extraction device, and the cavity further comprises one or more sorbent retention devices configured to retain the sorbent within the cavity.

Some examples of the disclosure are related to a method comprising coupling a sample vial to a sample extraction device via an external seal of the sample extraction device, wherein the sample vial includes a sample and a headspace gas, the sample comprising one or more of a solid and a liquid; drawing a vacuum in the sample vial through an internal seal of the sample extraction device, such that in the process of drawing the vacuum, the headspace gas is drawn through a sorbent included in the sample extraction device; and collecting the sample in the sorbent included in the sample extraction device while the vacuum is drawn in the sample vial.

Some examples of the disclosure are related to a method comprising coupling a sample vial to a sample extraction device via an external seal of the sample extraction device, wherein the sample vial includes a sample, the sample comprising one or more of a solid and a liquid; coupling a vacuum source to the sample extraction device; drawing a vacuum, with the vacuum source, in the sample vial through an internal seal of the sample extraction device for a first period of time, such that in the process of drawing the vacuum, the vacuum is drawn through a sorbent included in the sample extraction device; removing the vacuum source after the vacuum is drawn; after removing the vacuum source, collecting the sample in the sorbent included in the sample extraction device, for a second period of time, while the vacuum is held in the sample vial. Additionally or alternatively, in some examples, the method further includes after collecting the sample, decoupling the sample extraction device from the sample vial; coupling the sample extraction device to a column of a chemical analysis device; and passing a carrier fluid through a port on the sample extraction device seal and the sorbent of the sample extraction device and into the column of the chemical analysis device. Additionally or alternatively, in some examples, the chemical analysis device is configured to perform one or more of gas chromatography, gas chromatography—mass spectrometry, liquid chromatography, and liquid chromatography-mass spectrometry on the sample. Additionally or alternatively, in some examples, the method further includes after decoupling the sample extraction device from the sample vial and prior to coupling the sample extraction device to the column of the chemical analysis device and passing the carrier fluid through the internal seal of the sample extraction device: sealing the sample extraction device; an storing the sample extraction device. Additionally or alternatively, in some examples, the method further includes one or more of adsorbing and absorbing the sample into the sorbent while collecting the sample in the sorbent. Additionally or alternatively, in some examples, the method further includes eluting the sample from the sorbent using a solvent to form an extract; and inserting the extract into a chemical analysis device to perform one or more of gas chromatography, gas chromatography-mass spectrometry, liquid chromatography, and liquid chromatography-mass spectrometry on the extract. Additionally or alternatively, in some examples, the first period of time lasts until one or more of water and alcohol are eliminated from the sample. Additionally or alternatively, in some examples, the second period of time lasts until sufficient extraction of the liquid or solid sample has occurred, until equilibrium between the sample extraction device and the contents of the sample vial has been achieved, or until complete extraction of GC or LC compatible compounds from the sample in the sample vial has been achieved.

Although examples have been fully described with reference to the accompanying drawings, it is to be noted that various changes and modifications will become apparent to those skilled in the art. Such changes and modifications are to be understood as being included within the scope of examples of this disclosure as defined by the appended claims.

The invention claimed is:
1. A sample extraction device comprising:
 a cavity configured to contain a sorbent, the cavity having a first opening at an extraction end of the sample extraction device and a second opening at a valve end of the sample extraction device;
 a valve located at the valve end of the sample extraction device, the valve enabling selective opening and closing of the second opening of the cavity of the sample extraction device;
 an internal seal configured to selectively restrict fluid flow through the cavity, the internal seal disposed at the valve end of the sample extraction device;
 a plurality of external seals including a first external seal and a second external seal, the plurality of external seals disposed around an outside of the sample extraction device;
 a port that is fluidly coupled to the cavity and open to an environment external to the sample extraction device, wherein an opening of the port is located between the first external seal and the second external seal on the outside of the sample extraction device, wherein:

the plurality of external seals are configured to, during a sample collection process, form a seal between the sample extraction device and a sample vial, thereby sealing the port from the environment external to the sample extraction device,
 the valve at the valve end of the sample extraction device is configured to couple a vacuum source while a vacuum is drawn for a first period of time during the sample collection process, and
 the sorbent of the sample extraction device is configured to, after the vacuum is drawn, and while a vacuum is maintained in the sample vial, collect a sample for a second period of time during the sample collection process, and
 the sample extraction device is configured to be coupled to a desorption device during a desorption process,
 the valve at the valve end of the sample extraction device is configured to close during the desorption process; and
 the port is configured to accept a carrier fluid during the desorption process.

2. The sample extraction device of claim 1, wherein the sorbent is disposed within the cavity such that it is closer to the opening at the extraction end of the sample extraction device than it is to the valve end of the cavity.

3. The sample extraction device of claim 1, wherein the plurality of external seals comprises a fluoroelastomer seal or a perfluoroelastomer seal.

4. The sample extraction device of claim 1, wherein the external seal is disposed at a location on the sample extraction device such that, when the sample extraction device is inserted into the sample vial, the extraction end of the sample extraction device is inside a headspace gas in the sample vial.

5. The sample extraction device of claim 1, wherein the internal seal maintains a vacuum inside the sample vial after removal of the vacuum source from the sample extraction device.

6. The sample extraction device of claim 1, wherein the plurality of external seals are configured to form a seal between the sample extraction device and a chemical analysis device into which the sample extraction device is inserted.

7. The sample extraction device of claim 6, wherein the port is configured to facilitate flowing carrier fluid through the cavity and the sorbent and into the chemical analysis device during the desorption process.

8. The sample extraction device of claim 1, wherein the internal seal is configured to isolate sample, collected in the sorbent, from an environment of the sample extraction device after a sample extraction process.

9. The sample extraction device of claim 1, wherein the cavity is removably coupled to the sample extraction device, and the cavity further comprises one or more sorbent retention devices configured to retain the sorbent within the cavity.

10. A method comprising:
 during a sample collection process:
  coupling a sample vial to a sample extraction device via a plurality of external seals of the sample extraction device, the plurality of external seals including a first external seal and a second external seal, the plurality of external seals disposed around an outside of the sample extraction device between a first opening of a cavity of the sample extraction device at an extraction end of the sample extraction device and a second opening of a cavity of the sample extraction device at a valve end of the sample extraction device, wherein:
the sample vial includes a sample, the sample comprising one or more of a solid and a liquid, and
coupling the sample vial to the sample extraction device seals a port of the sample extraction device, the port being fluidly coupled to the cavity of the sample extraction device, an opening of the port being located between the first external seal and the second external seal,
coupling a vacuum source to a valve of the sample extraction device, the valve located at the valve end of the sample extraction device, the valve enabling selective opening and closing of the second opening of the cavity of the sample extraction device;
drawing a vacuum, with the vacuum source, in the sample vial through the valve of the sample extraction device for a first period of time, such that in the process of drawing the vacuum, the vacuum is drawn through a sorbent included in the cavity of the sample extraction device;
after drawing the vacuum, collecting the sample in the sorbent included in the sample extraction device, for a second period of time, while the vacuum is held in the sample vial; and
during a desorption process:
coupling the sample extraction device to a desorption device;
closing the valve at the valve end of the sample extraction device; and
introducing a carrier fluid to the sample extraction device through the port.

11. The method of claim 10, wherein the chemical analysis device is configured to perform one or more of gas chromatography, gas chromatography—mass spectrometry, liquid chromatography, and liquid chromatography-mass spectrometry on the sample.

12. The method of claim 10, further comprising:
after decoupling the sample extraction device from the sample vial and prior to coupling the sample extraction device to the desorption device and introducing the carrier fluid through the port of the sample extraction device:
sealing the sample extraction device; and
storing the sample extraction device.

13. The method of claim 10, further comprising one or more of adsorbing and absorbing the sample into the sorbent while collecting the sample in the sorbent.

14. The method of claim 10, further comprising:
eluting the sample from the sorbent using a solvent to form an extract; and
inserting the extract into a chemical analysis device to perform one or more of gas chromatography, gas chromatography-mass spectrometry, liquid chromatography, and liquid chromatography-mass spectrometry on the extract.

15. The method of claim 10, wherein the first period of time lasts until one or more of water and alcohol are eliminated from the sample.

16. The method of claim 10, wherein the second period of time lasts until a desired amount of extraction of the sample has occurred, until equilibrium between the sample extraction device and an inside of the sample vial has been achieved, or until complete extraction of one or more given compounds from the sample in the sample vial has been achieved.

* * * * *